(12) United States Patent
Hirshberg

(10) Patent No.: US 9,579,446 B2
(45) Date of Patent: Feb. 28, 2017

(54) MEMS BASED FILTER AND CATALIZER

(71) Applicant: David Hirshberg, Haifa (IL)

(72) Inventor: David Hirshberg, Haifa (IL)

( * ) Notice: Subject to any disclaimer, the term of this patent is extended or adjusted under 35 U.S.C. 154(b) by 542 days.

(21) Appl. No.: 13/645,522

(22) Filed: Oct. 5, 2012

(65) Prior Publication Data

US 2014/0099234 A1   Apr. 10, 2014

(51) Int. Cl.
*A61M 1/36* (2006.01)
*A61M 1/34* (2006.01)
*B01L 3/00* (2006.01)

(52) U.S. Cl.
CPC .......... *A61M 1/3687* (2013.01); *A61M 1/34* (2013.01); *B01L 3/502753* (2013.01); *A61M 2205/0244* (2013.01); *B01L 3/502738* (2013.01); *B01L 3/502761* (2013.01); *B01L 2300/0861* (2013.01)

(58) Field of Classification Search
CPC ........... B01L 3/202707; B01L 3/50273; B01L 3/502738; B01L 3/502753; B01L 3/502761; B01L 3/502769; B01L 2300/0864; B01L 2300/0816; B01L 2300/0861; B01L 2400/0638; B01L 11/0496
USPC .......... 137/599.01, 599.03, 601.04; 422/502, 422/503, 504
See application file for complete search history.

(56) References Cited

U.S. PATENT DOCUMENTS

| 2004/0005628 A1* | 1/2004 | Foster ............... B01L 3/502761 435/7.1 |
| 2005/0063872 A1* | 3/2005 | Foster ........................ 422/82.08 |
| 2005/0092662 A1* | 5/2005 | Gilbert et al. .................. 210/97 |
| 2009/0066315 A1* | 3/2009 | Hu ..................... G01N 15/1056 324/71.4 |
| 2009/0176230 A1* | 7/2009 | McBride et al. ................. 435/6 |
| 2010/0014068 A1* | 1/2010 | Padmanabhan et al. ........ 356/39 |
| 2010/0233799 A1* | 9/2010 | Takayama et al. ........ 435/305.2 |
| 2010/0303687 A1* | 12/2010 | Blaga et al. .................. 422/504 |
| 2011/0126910 A1* | 6/2011 | May .................... B01F 13/0059 137/1 |
| 2011/0151578 A1* | 6/2011 | Abate ............... B01L 3/502746 436/180 |

* cited by examiner

*Primary Examiner* — David C Mellon
*Assistant Examiner* — Pranav Patel

(57) ABSTRACT

The present invention provides a filter for separating particles and/or catalyzer for particle reaction in a fluid. The device comprising array of passageways fabricated on a die wherein the passageway size is controlled by actuators. The passageway size is monitored and the actuators controlling the passageway size are activated conditionally upon the passageway size monitoring. Using movable actuators the passageway can achieve passageway size that is less then the fabrication minimal resolution. Proper locating, setting and/or activation of the actuators create passageways that can perform filtration of particles, trapping of particles and catalyzing particles reaction.

17 Claims, 10 Drawing Sheets

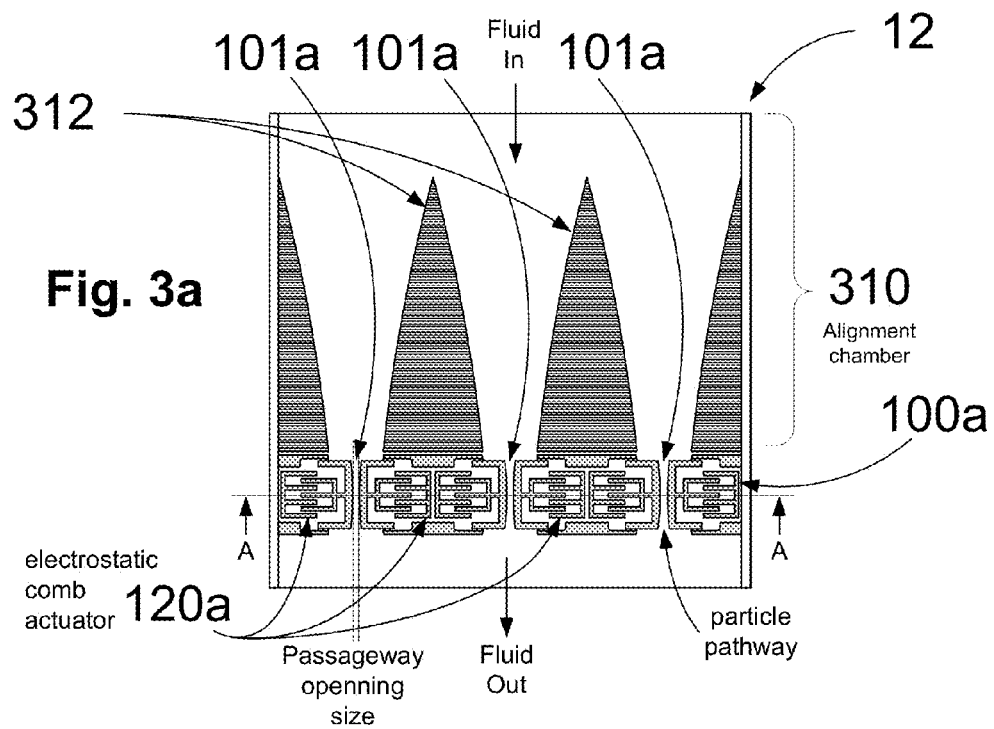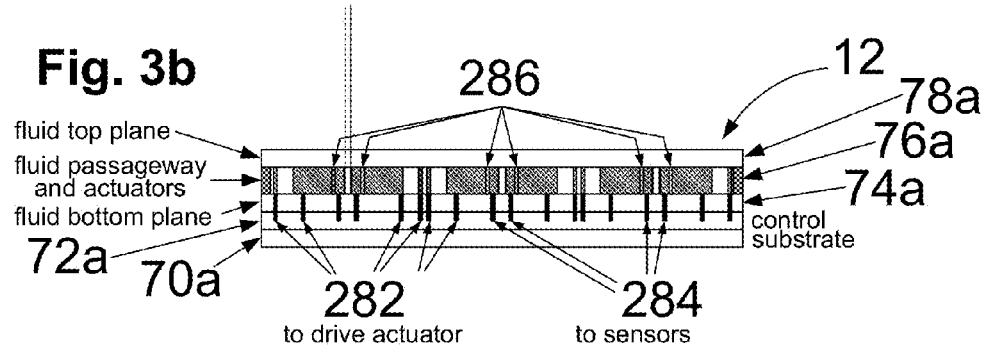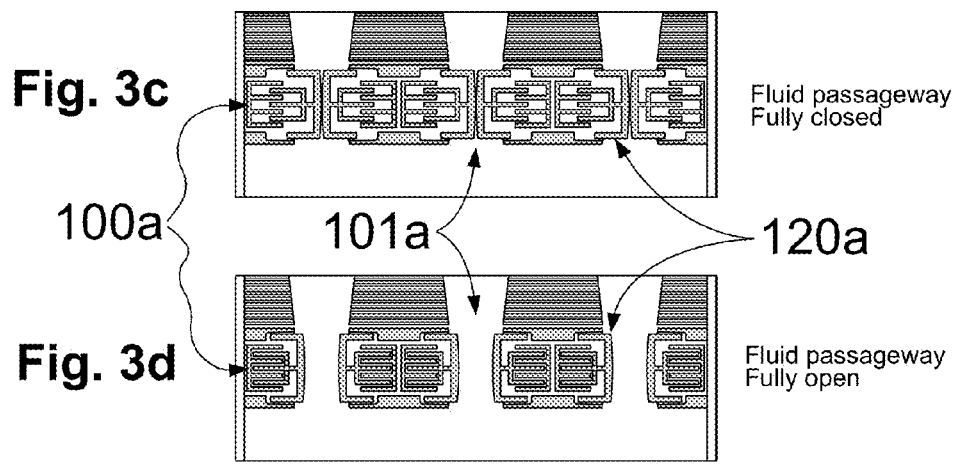

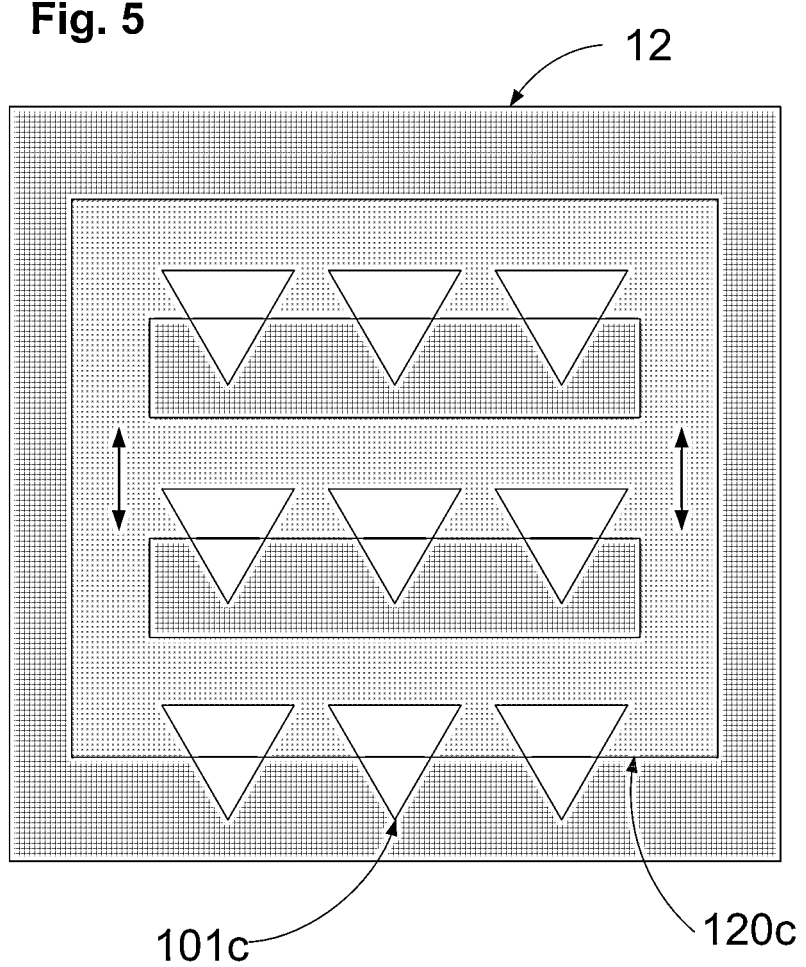

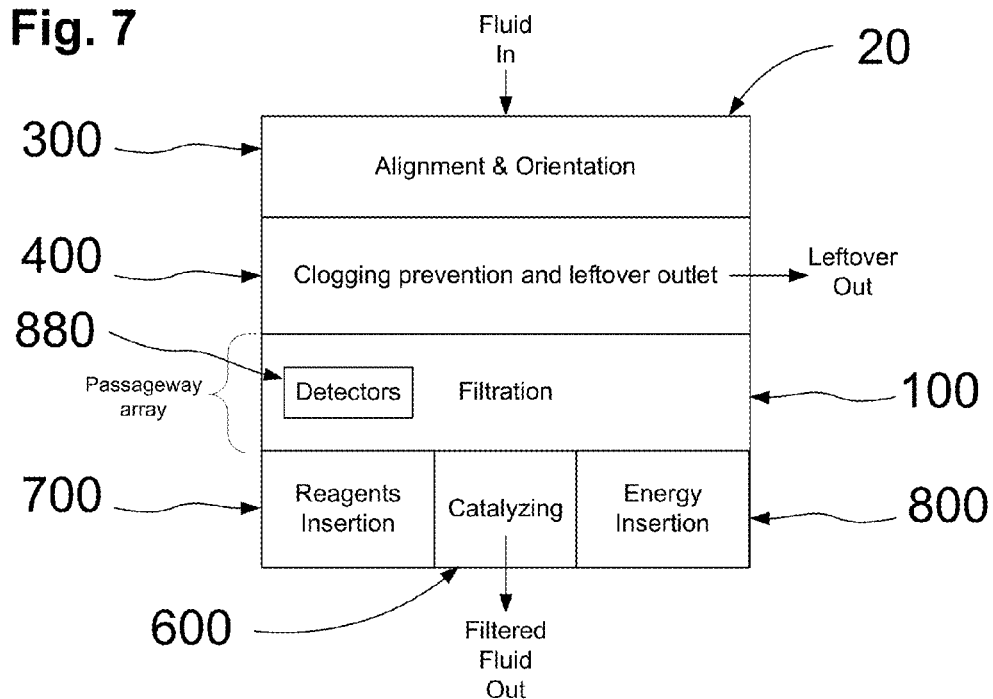
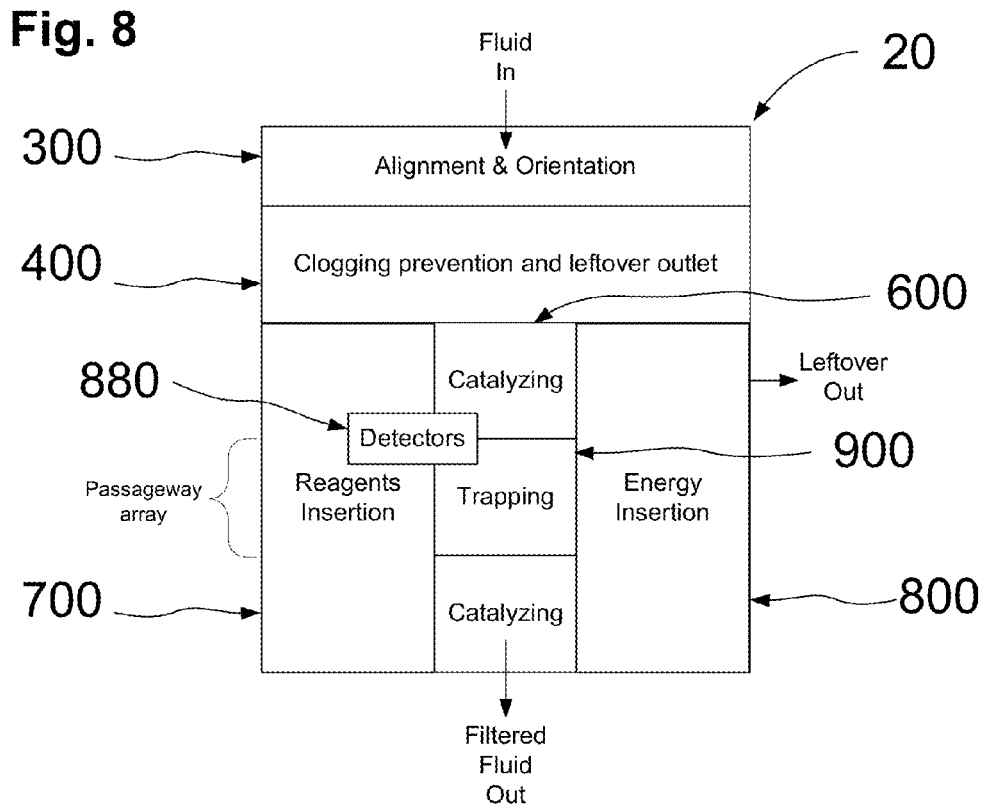

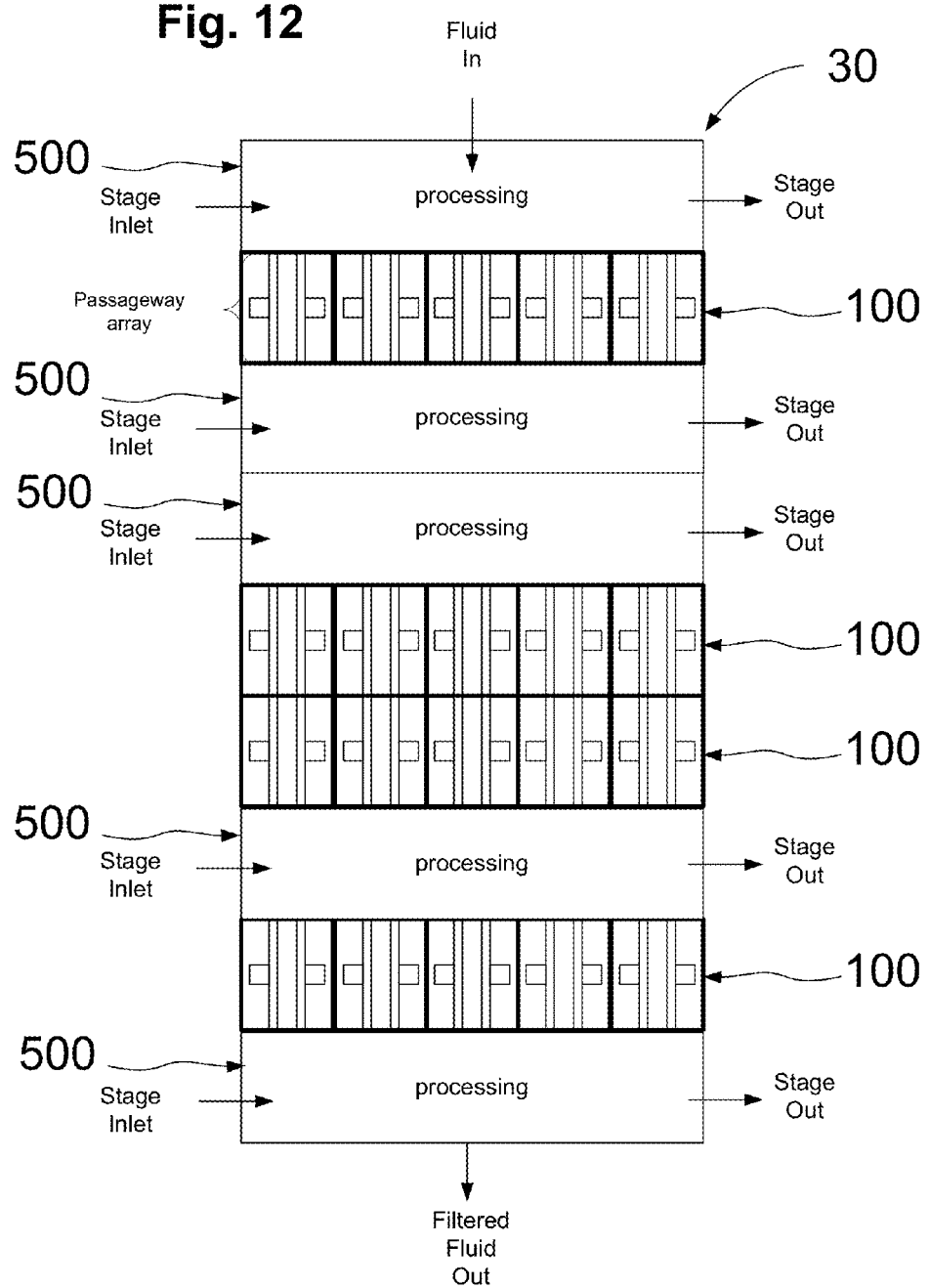

MEMS BASED FILTER AND CATALIZER

FIELD AND BACKGROUND OF THE INVENTION

The present invention, in some embodiments thereof, relates to particles filtration and catalysis and, more particularly, but not exclusively, to filters and catalyzers fabricated on a die.

Particles filters are components that separate particles in a fluid containing a mixture of particles. Particle can be as tinny as a single molecule with angstrom scale size thorough a bigger chain molecule like a protein in a nanometer scale size to a biological cell or organism or mineral grains such as dust with sizes range from micrometers to millimeters.

Filtration has many and varied applications, for example, filtration is used to clean the air in a clean rooms in the semiconductor industry. Filtration is also used in biological and medical application, for example, filtration of blood to analyze the contents of specific particles in it.

Catalysis is the act of promoting a chemical reaction between molecules. Generally speaking, the reaction can be combining two molecules to one or breaking a molecule into two smaller molecules. Complex reactions, like breaking the molecule to more then two products or transforming a pair of molecules to different pairs are also possible chemical reaction that can be catalyzed by a catalyzer.

SUMMARY OF THE INVENTION

The present invention, in some embodiments thereof, relates to particles filtration and catalysis fabricated on a die. The method comprises variable size passageways. The passageways are fabricated on a die by a known semiconductor fabrication process, such as photolithography and etching. The passageway size is controlled using actuators. The actuators are MEMS actuators that moves relative to the passageways and fabricated on the same die. The passageway size can be made as small as desired and even become fully closed. Optionally, the actuators are activated using close loop control circuits that have feedback from measuring the actual passageway size. A passageway size as low as few angstroms can be reached. Such resolution provides ability of filtration of fundamental molecules.

According to an aspect of some embodiments of the present invention there is provided a filter for separating particles in a fluid comprising array of passageways fabricated on a die wherein the passageway size is controlled by actuators.

According to some embodiments of the invention, the passageway size is monitored and the actuators controlling the passageway size are activated conditionally upon the passageway size monitoring.

According to some embodiments of the invention, the monitoring is done based on the capacitance measurement between pairs of the passageway walls or on the leakage current measurement between pairs of the passageway walls or on the amount of light or any electromagnetic signal with different wavelength that pass thorough the passageway or on any other measurable physical property that change its value with passageway size.

According to some embodiments of the invention, the combination between the actuators and the passageway are one or more of the actuators are controlling single passageway or a single actuator, alone or together with other actuators, shared plurality of passageways or any other many actuators to many passageways combinations.

According to some embodiments of the invention, actuators are MEMS actuators based on electrostatic, electromagnetic or piezoelectric forces.

According to some embodiments of the invention, the die is multilayer die and the layers are fabricated using at least one of evaporation, photolithography and etching.

According to some embodiments of the invention, the passageways are fabricated in one or more layers of the die plane or fabricated across all layers perpendicular to the die plane.

According to some embodiments of the invention, the filter comprises at least one of clog prevention subsystem, particles alignment subsystem, particle orientation subsystem, catalysis subsystem, inlets and outlets ports or any other pre filtration or post filtration processing subsystem.

According to some embodiments of the invention, the filter comprises pre filtration particle alignment subsystem and/or particle orientation subsystem using the mean of any combination of (1) electric field, (2) magnetic field, and (3) mechanical structures or forces.

According to an aspect of some embodiments of the present invention there is provided a catalyzer of reactions of particles in a fluid comprising array of passageways fabricated on a die wherein the passageway size is controlled by actuators and wherein the passageways are used for any combination of (1) filtering particles, (2) trapping particles, and/or (3) catalyzing particles reaction.

According to some embodiments of the invention, the trapping particles by the passageways is performed by setting the passageway size to enable only partial entry of a target particle to the passageway or performed by reducing the passageway size when a particle is inside the passageway.

According to some embodiments of the invention, the passageway size is monitored and the actuators controlling the passageway size are activated conditionally upon the passageway size monitoring.

According to some embodiments of the invention, the monitoring is done based on capacitance measurement between pairs of the passageway walls or on the leakage current measurement between pairs of the passageway walls or on the amount of light or any electromagnetic signal with different wavelength that pass thorough the passageway or on any other measurable physical property that change its value with passageway size.

According to some embodiments of the invention, the array of passageways is partitioned to groups wherein each group is acting in any given time as filter, traps, or catalyzer and the combination between the actuators and the group of passageway are one or more of the actuators are controlling single passageway or a single actuator, alone or together with other actuators, shared plurality of passageways or any other many actuators to many passageways combinations.

According to some embodiments of the invention, the actuators are MEMS actuators based on electrostatic, electromagnetic or piezoelectric forces.

According to some embodiments of the invention, the die is multilayer die and the layers are fabricated using at least one of evaporation, photolithography and etching.

According to some embodiments of the invention, the passageways are fabricated in one or more layers in the die plane or fabricated across all layers perpendicular to the die plane.

According to some embodiments of the invention, the catalyzer comprises at least one of clog prevention subsystem, particles alignment subsystem, particle orientation subsystem, particle energy insertion subsystem, reagent insertion subsystem, inlets and outlets ports or any other pre filtering or post filtration processing subsystem.

According to some embodiments of the invention, the particle energy insertion subsystem supply energy to the particles wherein the energy supplied at least in the form of kinetic energy, electric energy, magnetic energy, electromagnetic energy, heat energy or a combination of these.

According to some embodiments of the invention, a group of the actuators is delivering the kinetic energy to the trapped particles.

According to some embodiments of the invention, the catalyzer comprises particles detectors located in the passageways or adjacent to the passageways inlet or outlet.

According to an aspect of some embodiments of the present invention there is provided a method for processing of particles in a fluid comprising:
(a) providing array of passageways fabricated on a die wherein the passageway size is controlled by actuators;
(b) setting the actuators to create passageways that perform any combination of (1) filtering particles, (2) trapping particles, and/or (3) catalyzing particles reaction; and
(c) stream the fluid through the passageways.

According to some embodiments of the invention, the array of passageways is partitioned to groups wherein each group is acting in any given time as filter, traps, or catalyzer and the combination between the actuators and the group of passageway are one or more of the actuators are controlling single passageway or a single actuator, alone or together with other actuators, shared plurality of passageways or any other many actuators to many passageways combinations.

According to some embodiments of the invention, the processing comprises at least one of filtration of particles, sorting of particles, catalysis of particle reactions, clog prevention, particles alignment, particle orientation, energy insertion to particles, reagent insertion, inlets and outlets of fluids or any other fluid processing, wherein the processing is performed using dynamically activating different groups of actuators in time.

According to some embodiments of the invention, the passageway size is monitored and the actuators controlling the passageway size are activated conditionally upon the passageway size monitoring.

According to some embodiments of the invention, the passageway size is set by the actuators to be less then the die minimal fabrication resolution.

According to some embodiments of the invention, the processing is multistage processing and the processing is performed using multiple arrays of passageway fabricated on the same die and the fluid flow between stages of passageway processing.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Implementation of the method and/or system of embodiments of the invention can involve performing or completing selected tasks manually, automatically, or a combination thereof. Moreover, according to actual instrumentation and equipment of embodiments of the method and/or system of the invention, several selected tasks could be implemented by hardware, by software or by firmware or by a combination thereof using an operating system.

For example, hardware for performing selected tasks according to embodiments of the invention could be implemented as a chip or a circuit. As software, selected tasks according to embodiments of the invention could be implemented as a plurality of software instructions being executed by a computer using any suitable operating system. In an exemplary embodiment of the invention, one or more tasks according to exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 3a is a top view of a die in accordance with an exemplary of in plane filter embodiment of the current invention;

FIG. 3b is a cross section of the die illustrated in FIG. 3a;

FIG. 3c is an illustration of the actuators illustrated in FIG. 3a in fully closed position;

FIG. 3d is an illustration of the actuators illustrated in FIG. 3a fully open position;

FIG. 4b is a cross section of the die illustrated in FIG. 4a;

FIG. 5 is a top view of a die in accordance with a single actuator shared by all passageways exemplary embodiment of the invention;

FIG. 6b is a cross section of the die illustrated in FIG. 6a;

FIG. 7 is a conceptual block diagram of a catalyzer in accordance with the current invention;

FIG. 8 is a conceptual block diagram of another type of catalyzer in accordance with the current invention;

FIG. 9b is a cross section of the die illustrated in FIG. 9a;

FIG. 10b is a view on the initial stage;
FIG. 10b is a view on the trapping stage;
FIG. 10c is a view on the catalysis stage;
FIG. 10d is a view on the initial stage;
FIG. 11b is a cross section of the die illustrated in FIG. 11a;
and
FIG. 12 is a conceptual block diagram of a multi process fluid processing system in accordance with the current invention.

DESCRIPTION OF SPECIFIC EMBODIMENTS OF THE INVENTION

Figure 1:
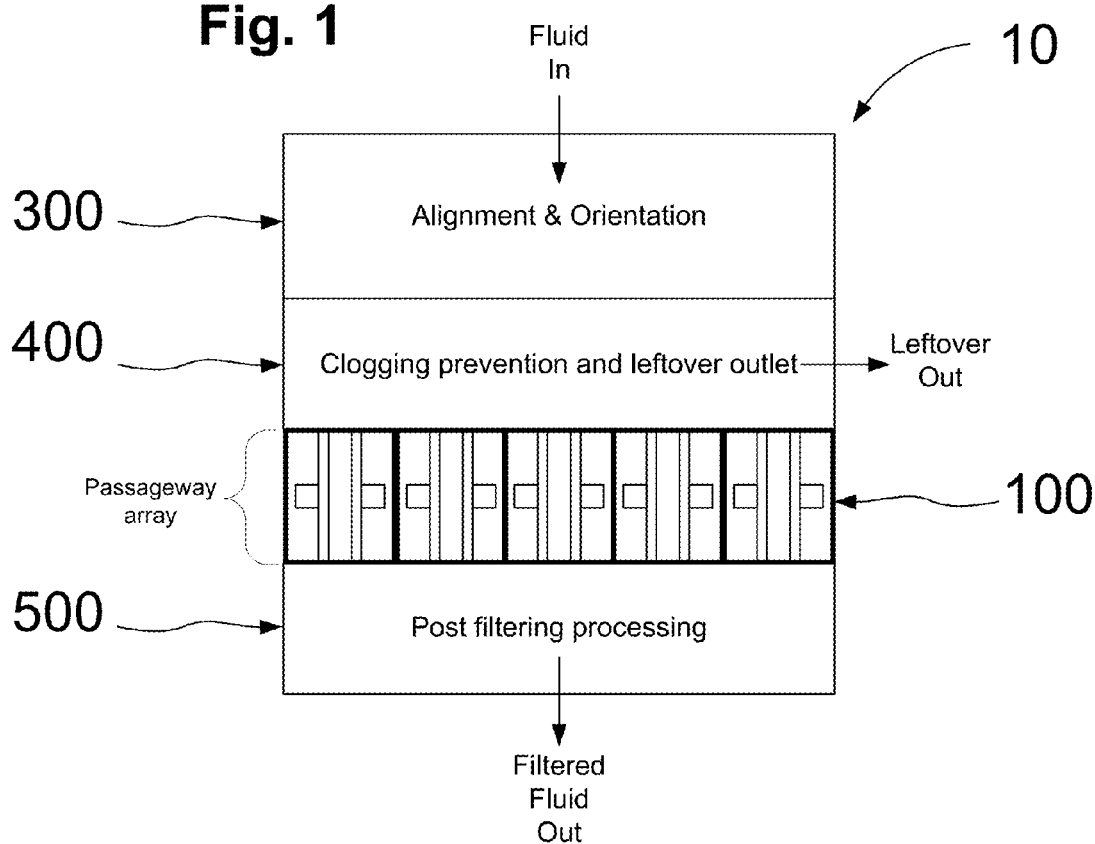
FIG. 1 is a conceptual block diagram of a filter in accordance with the current invention.

The present invention, in some embodiments thereof, relates to particles filtration and catalysis and, more particularly, but not exclusively, to filters and catalyzers fabricated on a die.

As used herein, the term die means a flat multilayer surface fabricated by processes used mainly in the semiconductor industry. Fabrication processes comprise but not limited to evaporation, photolithography, etching, vapor deposition, etc. The die materials comprises but not limited to silicon, germanium, carbon, gallium arsenide or any other semiconductor materials, polymers, metals such as gold, copper, aluminum, silver, ceramics material such as alumina, silicon dioxide, zinc oxide, oxides, Nitrides, carbides, yttrium barium copper oxide or any other material that can be used in die fabrication processes.

As used herein, the term particle is a molecule, a chain of molecules, a biological cell or organism, or mineral grains such as dust. Sizes of particle can be in the range from angstroms to millimeters. The particle has some bonding connection between its ingredients and it can be rigid or flexible.

As used herein, the term fluid is a gas mixture, such as air, or a liquid mixture, such as blood or mineral water. The fluid mixture can be a solution or non soluble mixture.

The most popular filters in use today are filters that use porous or fibber based material. Such filters do not have precise particle passageway size so they can only have rough filtration characteristics. Fixed passageway size filters are done by precise fabrication. Micro or nano fabricated filters fabricated by current semiconductor fabrication processes are known in the art, see for example U.S. Pat. No. 5,651,900 entitled "Microfabricated Particle Filter", by Keller et al. Some applications have precise particle passageway size but the particle passageway size is usually limited by the fabrication technology. Such filters are less flexible and need to be designed and manufactured specifically for each application which makes them more costly and less practical.

As used herein, the term passageway means a hallow volume that particles with a limited size can pass through from one side to the other side of the passageway.

As used herein, the term passageway size means an indicator for the maximal size of particles that can pass the passageway. For example, for a passageway shape of circle or cylinder, the diameter fully describes the passageway size. For rectangular shape passageway both length and width are needed. In general case, both the passageway and the particle are 3D objects and all dimensions of the particle and the passageway as well as the orientations and elasticity of both passageway and particle affect the actual size of the particle that can pass through the passageway.

U.S. Pat. No. 6,838,056 entitled "Method and Apparatus for Sorting Biological Cells with a MEMS Device", by Foster teach a die based fluid processing using MEMS actuator but the actuators are used only as a valves that direct particles to flow between two possible passageways. The current invention is using actuators to control passageway size, to trap particles in passageway and to transfer kinetic energy into particles to promote reaction, i.e. to catalysis.

In an exemplary embodiment of the invention, a new flexible and accurate, filtration method and device are provided. The invention provides many new ways, abilities and applications in fluid filtration. The filtration method comprises variable size passageways. The passageways are fabricated on a die by a known semiconductor fabrication process, such as photolithography and etching. The passageway size is controlled using actuators. The actuators are MEMS actuators that moves relative to the passageways and fabricated on the same die. This method enables the creation of passageways sizes that are much smaller then the fabrication process capabilities. The passageway size can be made as small as desired and even become fully closed, i.e., blocking all particles. The smallest size resolution is depend on the accuracy of control of the actuators. Optionally, the actuators are activated using close loop control circuits that measure the actual passageway size. Passageway size may be measured by capacitance measurement on the actual gap between passageway walls. Leakage current or light intensity or any other physical property that is varied in accordance with the passageway size may be used. A passageway size as low as few angstroms can be reached. Such resolution provides ability of filtration of fundamental molecules.

As used herein, the term actuator means an element that is able to move relative to the die upon instruction. Common actuators, also known as MEMS actuators, are electrostatic, e.g., comb actuator, electromagnetic, piezoelectric and thermal. The move instruction is usually an electric signal such as voltage or current.

In an exemplary embodiment of the invention, a pre filter orientation process/element/subsystem is implemented. Such element enables accurate filtration of non symmetric particles/molecules. In an exemplary embodiment of the invention, a clogging prevention process/element/subsystem is implemented. Clogging prevention prevents clogging particles to block the filter or alternatively evacuate blocking particles from the filter.

In an exemplary embodiment of the invention, the passageway size is programmable and changed during filter operation to provide filtration of different particles with the same filter in different times, or to release clogging in specific stage on time or to switch on and off the filtration.

Before explaining at least one embodiment of the invention in detail, it is to be understood that the invention is not necessarily limited in its application to the details of construction and the arrangement of the elements and components and/or methods set forth in the following description and/or illustrated in the drawings and/or the Examples. The invention is capable of other embodiments or of being practiced or carried out in various ways.

Referring now to the drawings, FIG. 1 illustrates a conceptual block diagram of the filter in accordance with the current invention. The core of filter 10 is array of passageways 100. The conceptual block diagram of each passageway element is provided in FIG. 2. The fluid enters an optional alignment and orientation chamber 300 that is provided to align and orient the particles to be filtered. At the inlet of passageway array 100 an optional clogging prevention and leftover outlet subsystem 400 is provided. The particles that are too big to go through the filter passageways are drained to the leftover outlet. The fluid and the particles that pass through passageway array 100 are further processed by optional post filter processing subsystem 500 and then flow out of the filter.

Figure 2:
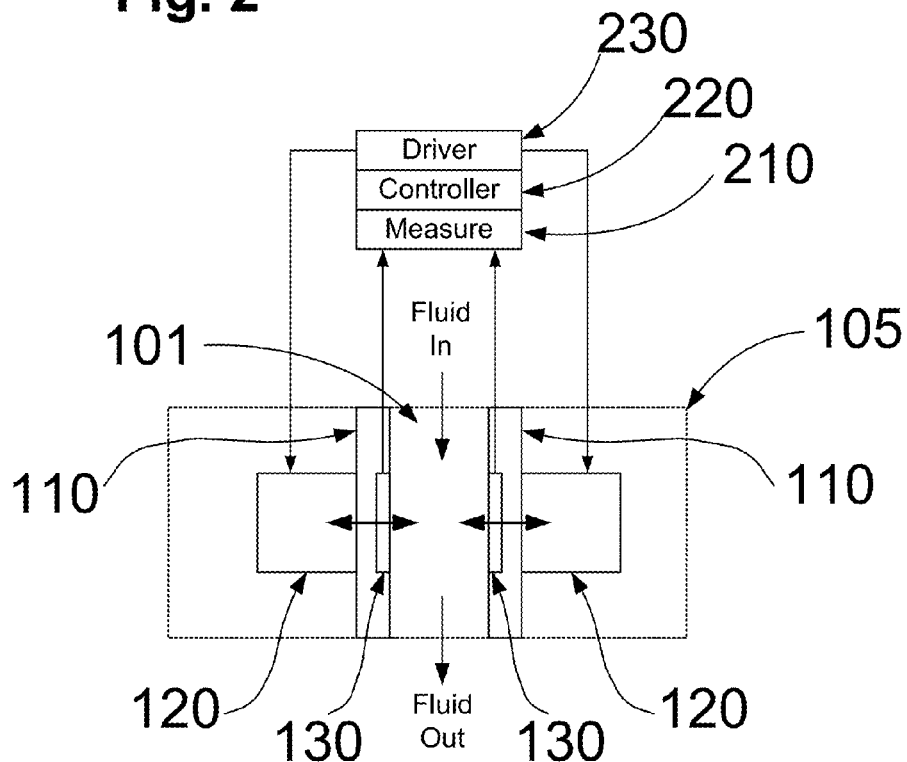
FIG. 2 is a conceptual block diagram of a single passageway element of a passageway array in accordance with the current invention.

Reference is made now to FIG. 2. FIG. 2 illustrates a conceptual block diagram of a single passageway element 105 of passageway array 100 in accordance with the current invention. Passageway 101 is a hallow volume limited by movable walls 110. Walls 110 are connected to actuators 120. Driver 230 drives actuators 120. Passageway walls 110 comprise sensors 130 that are connected to measurement unit 210. Measurement unit 210 measure the gap size of passageway 101. The measurements from measurement unit 210 are provided to controller 220 that instruct driver 230 to drive actuators 120 that moves passageway walls 110. Controller 220 controls the passageway according to the requirements of the system. Optionally, controller 220 uses a close loop control scheme with real time feedback from measurement unit 210 to maintain an accurate passageway size.

Reference is made now to FIGS. 3a-3d. FIGS. 3a-3d illustrate a simplified exemplary embodiment of the invention with an actual elements fabricated on a die. The fluid flow in this case is parallel to the surface of the die. Such arrangements are referred hereinafter as "in plane" implementation. In other embodiments of the invention the fluid flow is perpendicular to the plane of the die. Such implementations are referred as "out of plane" implementations.

Reference is made now to FIG. 3a. In FIG. 3a, a top view of the die is illustrated. The fluid to be filtered flows from top of die 12 to the bottom of die 12. First, the fluid passes an alignment chamber 310. Additionally or alternatively, particles/molecules are aligned and orientate by electric or magnetic fields. For example if target molecules have electric or magnetic dipoles applying a field in the proper direction will rotate the molecule to a desired orientation. Next, the fluid passes through array of controllable passageways 100a. For illustration clarity, only three passageways 101a are illustrated in the figure. Typically, hundreds to thousands passageways will be manufactured on a single die. Passageways 101a width is controlled by actuators 120a that move the passageway edges inwards and outwards. The actuators shown in the figure are electrostatic comb actuators. Additionally or alternatively, other types of actuators such as magnetic or piezoelectric can be used.

FIG. 3b illustrates a cross section of die 12 across line AA illustrated in FIG. 3a. Die 12 contains five major layers. The bottom layer is substrate 70a. Silicon substrate is preferred but other substrate may be used. Above the substrate, a control layer 72a is fabricated. The control layer may comprise several sub layers. The control layer comprises connecting conductors to the actuators 282. Optionally, the control layer contains connecting conductors to the passageway sensors 284. Passageway 101a width is monitored by measurement of the capacitance between the two sides of the passageway edges. The capacitance is inversely proportional to the distance of the passageway width, so when the width is small the capacitance increase significantly. This fact allows achieving a very good resolution in measurement small gaps and accurate control of the passageway width in very small sized is achieved. Optionally, to enable accurate measurement of the capacitance, an insulator 286 are inserted between the comb part of the actuator and the passageway walls.

Optionally, control layer 72a implements the full control system of the filter and comprises actuator drivers and measurement means including transistors, digital and analogue circuits all implemented inside layer 72a.

The third layer is fluid bottom plane 74a. This surface is preferably made of $SiO_2$ or any other chemically non reactive compound. Layer 74a is used as the floor of passageways 101a and also contains conductive pass through, i.e., vias, for driving the actuators and measuring the passageway width.

The fourth layer 76a contains the actuator and the passageways structure as illustrated by the top view of FIG. 3a. Each passageways 101a surrounded be two actuators and the passageways 101a width, the gap, become wider when actuator pull the passageways 101a edges outwards and become narrower when the actuators push the passageways 101a edges inwards. The top layer 78a closes the filter passageways from the top side. Layer 78a acts as the ceiling of the passageway and captures the fluid inside the filter cavity.

FIG. 3c and FIG. 3d illustrate the actuators 120a and passageways 101a in fully closed and fully open positions respectively.

The previous exemplary embodiments of FIG. 3a-FIG. 3d implements in plane filter with one dimensional array of passageways. Next, a perpendicular to plane two dimensional passageway array embodiments is illustrated.

Figure 4A:
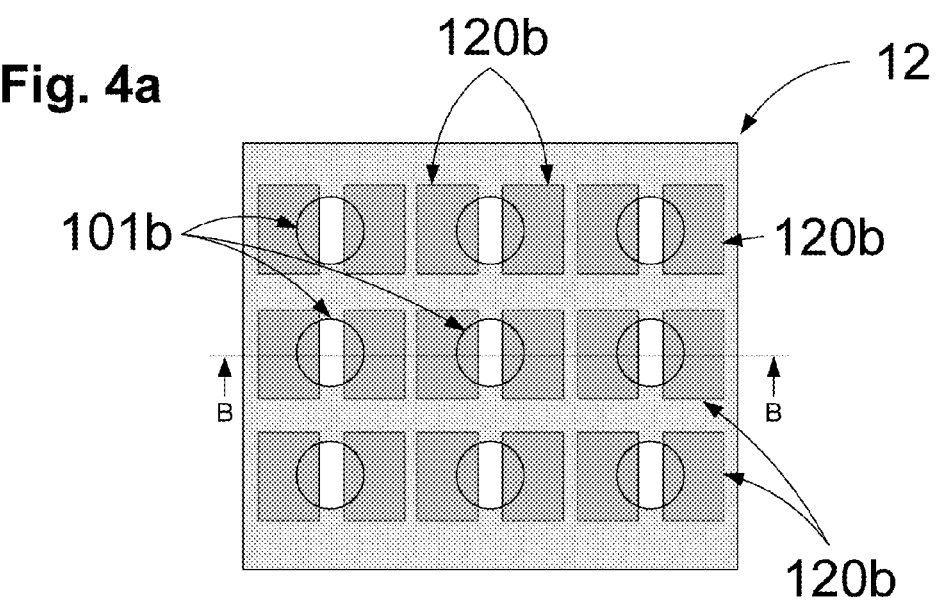
FIG. 4a is a top view of a die in accordance with an exemplary of out of plane filter embodiment of the current invention.
Figure 4B:
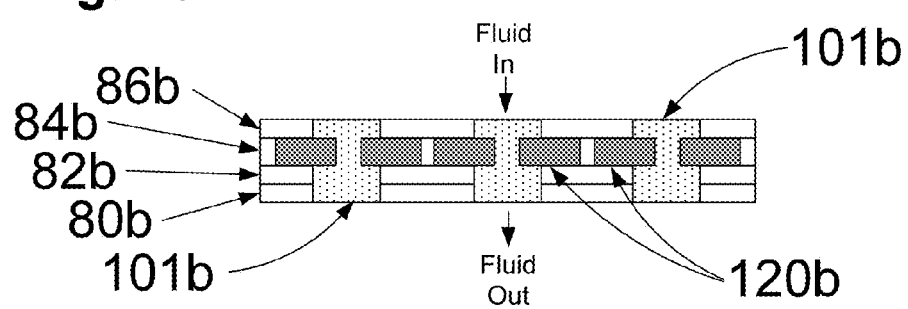

Reference is made now to FIG. 4a. FIG. 4a illustrates a top view of the die. The fluid to be filtered flows from top of die to the bottom of die perpendicular to the die plane. Die 12 contains a 2D array of passageways 101b. Passageways 101b are fabricated by performing pores through all layers of the die, e.g., by using etching fabrication techniques. The passageway passes through die 12. Each passageway 101b is surrounded by two actuators 120b. Each actuators 120b pair act as a sliding door that can partially or fully block passageway 101b. For clarity the full detail of actuators 120b implementation is not given in the figure and they are denoted by rectangular. Electrostatic comb actuator implementation similar to the one illustrated in FIG. 3a may be used. Other electrostatic actuators or any other actuator scheme can be used as well. Actuators 120b are implemented in internal layer as illustrated next in FIG. 4b. Reference is made now to FIG. 4b. FIG. 4b illustrates a cross section of die 12 across line BB illustrated in FIG. 4a. Die 12 have four principle layers. Substrate layer 80b is the bottom layer. On top of substrate 80b a control layer 82b is fabricated. As in previous embodiment control layer 82b can be simple connection matrix to another component that performs the actual control and measurements or it can contain all electric circuits inside die 12. Note that control layer 82b is not a full plane but a plane with pores. The existence of pores reduce the effective area of the layer but as long as an elements, e.g., wires and transistors, are smaller then the area between the pores any control circuit can be implemented on control layer 82b. On top of control layer 82b an actuators layer 84b is fabricated. The size reduction or blocking operation of actuators 120b on passageway 101b is clearly illustrated in this figure view. Actuators 120b are move inside this layer to provide variable pore size from fully close passageway to fully open passageway.

In an exemplary embodiment of the invention, three dimensional shape passageways are fabricated using a stack of independent actuators layers.

In an exemplary embodiment of the invention, the number of actuators per passageway is one. In an exemplary embodiment of the invention, the number of actuators per passageway is three or more. In an exemplary embodiment of the invention, a single actuator is shared between several passageways.

In an exemplary embodiment of the invention, passageway cross section is fabricated as rectangle, ellipse or any other geometrical shape.

Reference is made now to FIG. 5. FIG. 5 illustrates an exemplary embodiment of the invention, with a triangle passageway cross section and a single actuator shared by all passageways. Triangle passageways 101c are controlled by a single actuator 120c that shared between all passageways. When actuator 120c is pulled to the top of the figure all passageways are fully open and when actuator 120c is pushed to the bottom all passageways are fully closed. In any actuator 120c position the shape of the passage cross section is a triangle but the length of the triangle sides is different.

Clogging Prevention

One of the biggest problems in filtration is clogging. Clogging accurse when a particle is too big to pass the passageway and stack in front of the passageway or inside the passageway. The less problematic problem is when the particle is larger the size of the passageway. In this case the particle is stack in the passageway inlet and the passageway is blocked. Since the invention provides variable size passageways the filter controller can clean itself by applying "cleaning cycles". In cleaning cycle the passageways are set to fully open state so the clogging particles that clog the passageways are swept out through the passageway. Additionally or Alternatively, A clogging prevention mechanism is implemented to solve the problem of clogging during normal operation and without applying cleaning cycles. Such clog prevention mechanism may eliminate the need to perform periodically cleaning cycles or increase the time duration between cleaning cycles. An exemplary embodiment of cleaning mechanism for perpendicular to the die plane filter is illustrated in FIGS. 6a and 6b.

Figure 6A:
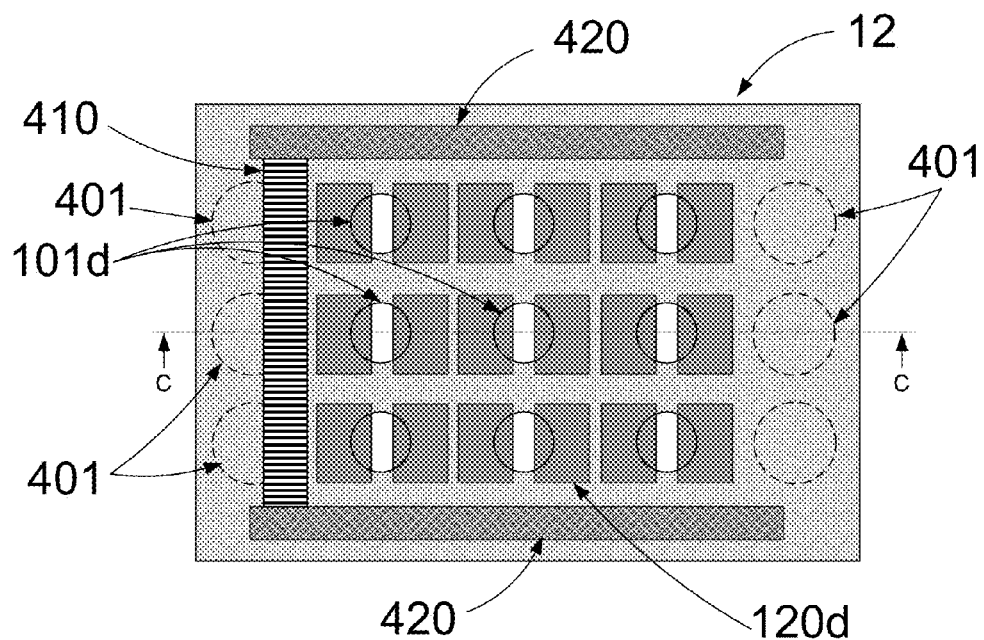
FIG. 6a is a top view of a die in accordance with an exemplary of a clogging prevention mechanism embodiment of the invention.

Reference is made now to FIG. 6a. FIG. 6a illustrates a top view of an exemplary embodiment of the invention with perpendicular to the die plane filter and clogging prevention mechanism. Die 12 comprises the array of passageway 101d controlled by actuators 120d similar to the embodiment of FIG. 4. In addition, cleaning passageways 401 for evacuating clogging particles are provided in the left and the right edges of die 12. The pores of cleaning passageways 401 are wider then the filter passageways 101d so all clogging particles pass through cleaning passageways 401. A sliding cleaning bar 410 is sliding in a special clog cleaning layer located on top of the actuators layer, illustrated in FIG. 6b. Sliding cleaning bar 410 is sliding of the die plane using step actuator sliders 420 located at the edges of die 12. Sliding cleaning bar 410 is continuously sliding from edge to edge of die 12, from left to right the back from right to left. When passing over passageways 101d sliding cleaning bar 410 pushes the clogging particles away from the passageway inlet and when bar 410 reaching the edges, the clogging particles are exhausted to the cleaning passageways 401.

Figure 6B:
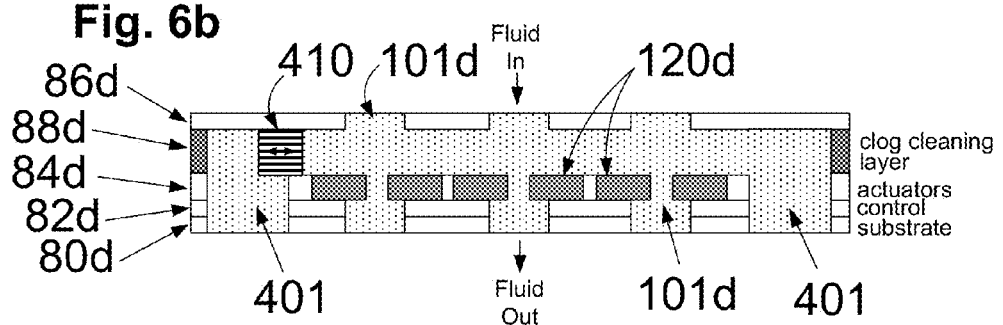

Reference is made now to FIG. 6b. A cross section of die 12 across line CC illustrated in FIG. 6a. The bottom layer is substrate 80d. Above the substrate, a control layer 82d is fabricated. The implementation details of control layer 82d are similar to the control layer in previous embodiments. In addition to controlling and driving actuators 120d, control layer 82d optionally contains circuitry to control and drive step actuator sliders 420. The third layer is actuators layer 84d is similar to layer 84b illustrated in FIG. 4b. Above actuators layer 84b, clean clogging layer 88b is fabricated. This layer contains cleaning bar 410 that slides over actuators 120d. This layer also contains part of step actuator sliders 420 and the inlet to cleaning passageways 401. Top layer 86d covers the cavity of filter 12.

In an exemplary embodiment of the invention, similar mechanism for cleaning clogging particles is used in in-plane filter embodiment.

Catalyzing

Having a controlled size passageways build in a fabricated die, open the door for other manipulations on participles that can be done in conjunction with the fact that the particle is passing through the passageway. Few angstroms passageway size enable catalyzing chemical reactions as shown next. In the following exemplary embodiments of the invention a new flexible and accurate catalysis schemes are provided. The catalyzer die is fabricated with particle/molecule filter passageways or traps that change their size via MEMS actuators that move relative to the die in similar fashion to what have been disclosed before.

As used herein, the term trap means a passageway that is designed and set to capture a particle/molecule in specific place for a specified duration.

As used herein, the term catalyzer is a device that performs the act of promoting a reaction between particles. The reaction can be a chemical reaction of combining two molecules to one, breaking a molecule into two smaller molecules or complex chemical reactions, such as, reaction involving more then two reactants or products. In addition, the term catalyzer is used herein to describe a device that performs the act of promoting breaking or combining particles that are not a plain molecules and the break or combine of those particle are not usually classified as a chemical reaction per se.

Reference is made now to FIG. 7. FIG. 7 illustrates a conceptual block diagram of the catalyzer in accordance with the current invention. catalyzer 20 comprises alignment & orientation chamber 300, clogging prevention and leftover outlet subsystem 400 and filtration chamber using passageway array 100 similar to the embodiment illustrated in FIG. 1. The particles/molecules that pass through the filter are the target particles/molecules for reaction. The filtered, i.e., target particles/molecules pass to catalyzing chamber 600. Additionally or alternatively, catalyzing chamber 600 is overlapping the filtration passageway and the catalysis occurs during the particle pass through the passageway. The reaction can be either a break of the particle/molecule or combine with other particle molecule. In the case of combine reaction other reagents are needed to participate and optionally those reagents are inserted to the canalization chamber using reagents insertion subsystem 700. The reaction can be a combination of both break and combine reactions. To catalyze the reaction some energy need to be supplied. The energy to promote the reaction is supplied by energy insertion subsystem 800. The energy to promote the reaction can be mechanical/kinetic energy, electromagnetic energy, e.g., RF/IR/light/UV, electric or magnetic energy. It is well known that for some chemical reaction a very specific amount of energy is needed with the right momentum and in the right time. Using the current invention the place of reaction is well defined since the particles is going through the passageways. In an exemplary embodiment of the invention, energy insertion subsystem 800 comprises MEMS actuator to insert kinetic energy to the particles. Additionally or alternatively a heater element or piezoelectric element is inserted in the passageway.

In an exemplary embodiment of the invention, energy insertion subsystem 800 comprises electromagnetic source radiated to passageway or passageway inlet or passageway outlet. Electromagnetic source comprises LEDs, Lasers, VCSELs, Antenna elements or any other EM emitting devices.

In an exemplary embodiment of the invention, energy insertion subsystem 800 comprises a source of electric or magnetic field induced to the passageway or passageway inlet or passageway outlet. The electric or magnetic fields are designed to transfer energy to the target particles.

Optionally, to achieve, when needed, the accurate time to supply the energy, detectors 880 are integrated in catalyzer 20 to detect when a particle is passing through the passageway. The detection can be based on same capacitance measurement of the passageway gap that change when particle is on the gap, or detection of the electromagnetic wave that pass through the passageway (the particle may absorb some of the light), or sensing the particle mass using a sensitive cantilever deployed in the passageway, or any other mean that can sense the existence and optionally the type of the particle in the passageway.

In an exemplary embodiment of the invention, kinetic energy is supplied by energy insertion subsystem 800 using MEMS actuators in a similar fashion as it is used to perform the passageway. Additionally or alternatively, the mechanical energy insertion is performed with the sane actuator used for filtration, so a single actuator performs both passageway sizing and kinetic energy transfer operations.

Reference is made now to FIG. 8. Catalyzer 20 comprises alignment & orientation chamber 300 and clogging prevention and leftover outlet subsystem 400 similar to the embodiment illustrated in FIG. 1. The same mechanism of the movable actuator passageways is be easily transformed to a trap mechanism. If the passageway opening is set to a size that is slightly smaller then the target particle, the particle can trap on the passageway inlet. Alternatively, trapping can be performed by closing the passageway when a particle is in the passageway. In an exemplary embodiment of the invention, catalyzer 20 comprises trapping array 900. The movable actuators in the trap enable the trap to be used multiple times be opening the trap and releasing the trapped particle and then set again the trap by close the trap again. The MEMS actuators allow trap size to reach sub nanometer sizes even sizes down to few atoms molecules size, is possible. Using MEMS actuator, catalyzing chemical reaction of any small size molecule is possible. When the particle is holed by the trap the catalysis process can be performed. Driving the trap actuator is done using close loop control as demonstrated previously and illustrated in FIG. 2. Catalyzer 20 comprises catalyzing chamber 600 in front to the trapping array 900. The particles that trapped are catalyzed one that chamber. To promote the reaction reagents insertion subsystem 700 and energy insertion subsystem 800 are provided. Additionally or alternatively, catalyzing chamber 600 is overlapping the trap and the catalysis occurs during the particle is in the trap. Additionally or alternatively, catalyzing chamber 600 is located adjacent to the trap outlet and the catalysis occurs when the particle exit the trap. Catalyzer 20 comprises detectors 880 to detect when a particle is trapped or passing through the trap/passageways.

All options describe above for implementation of energy insertion subsystem 800 and detectors 880 are possible in this embodiment as well.

The implementation of all components in a single a die enables integration of several steps of filtration, reagent delivery and reactions to provide complex chemical system capabilities.

The following examples illustrate exemplary simplified embodiments of the catalyzer invention and demonstrate the actual elements fabricated on a die using semiconductor fabrication methods. The fluid flow as in the filter case is either in plane implementation or out of plane, i.e., perpendicular to the plane of the die.

Figure 9A:
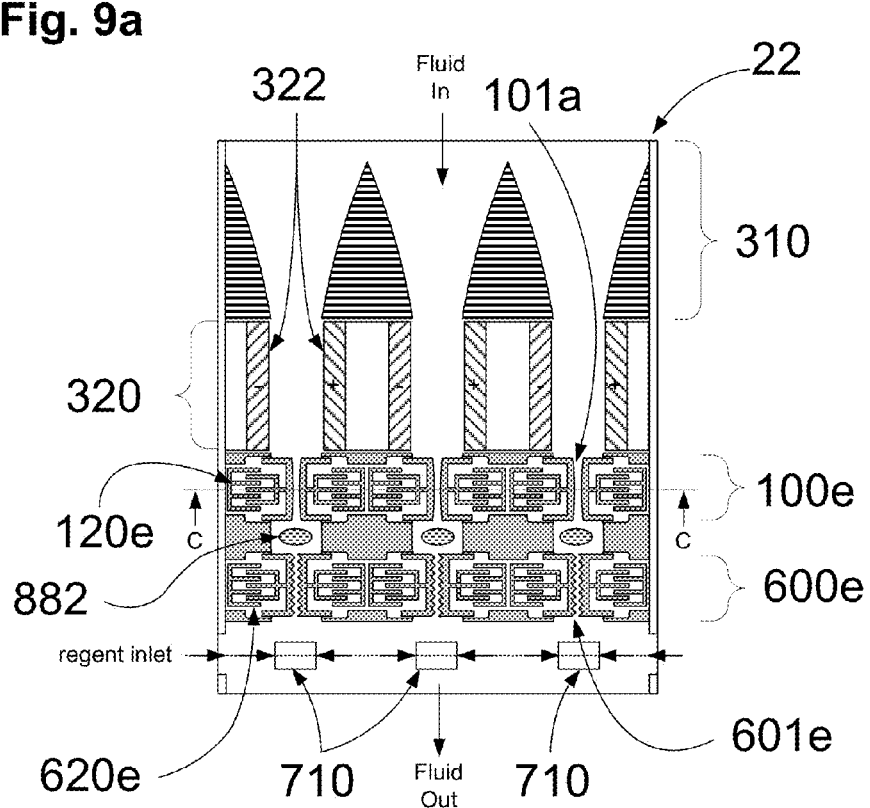
FIG. 9a is a top view of a die in accordance with an exemplary of in plane catalyzer embodiment of the current invention.
Figure 9B:
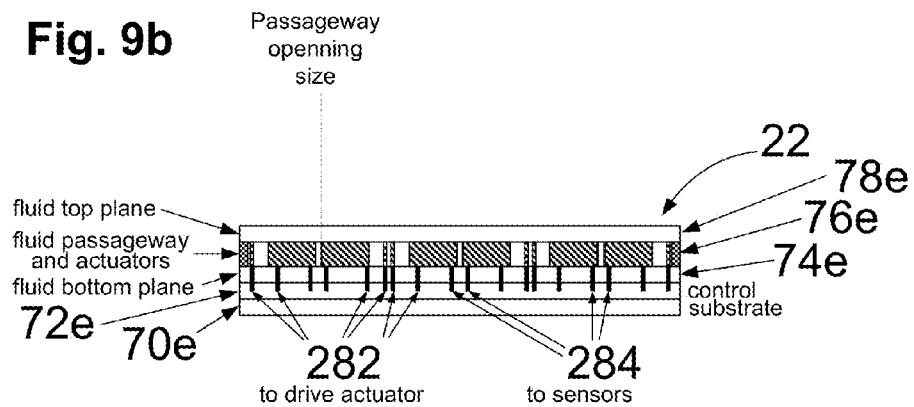

FIGS. 9a-9b illustrate an exemplary simplified embodiment of the catalyzer invention with an actual elements fabricated on a semiconductor die. The fluid flow in this embodiment is in plane.

Reference is made now to FIG. 9a. In FIG. 9a, a top view of the die is illustrated. The fluid flows from top to bottom. First, the fluid passes an alignment chamber 310. Afterwards, the fluid pass through orientation chamber 320 that rotate molecule with electric dipole in accordance with the electric fields. For example if target molecules have electric or magnetic dipoles applying a field in the proper direction will rotate the molecule to the desired orientation to pass through three passageways. Orientation chamber 320 contains rods 322 that are charged with positive and negative charges. Next, the fluid passes through array of controllable passageways 100e. The passageways are similar to the passageways that were demonstrated in FIG. 3a. For clarity, only three passageways 101e are illustrated in the figure. Typically, hundreds to thousands passageways will be manufactured on a single die. Filtration passageways 101e width is controlled by actuators 120e that move the passageway edges inwards and outwards. The actuators shown in the figure are electrostatic comb actuators. Additionally or alternatively, other types of actuators such as magnetic or piezoelectric can be used. The particles that pass the filtration of passageways 100e go through a second array of passageways, catalyzing passageways array 600e. Catalyzing passageways 601e are controlled by the catalyzing actuators 620e. Catalyzing actuators 620e are vibrating in specified frequency in order to provide the molecule that passes through the passageway a kinetic energy with the right momentum to excite electrons in the molecule to higher energy levels. Additionally or alternatively, the provided kinetic energy breaks the molecule to two or more smaller molecule. Optionally, Detectors 882 are located between filtration passageways 101e and catalyzing passageways 601e. The detector can sense the existence of a particle exiting filtration passageways 101e and entering catalyzing passageways 601e and trigger the catalyzing actuators 620e. To complete the reaction in this exemplary embodiment of the invention, reagent inlets 710 are located in the outlets of catalyzing passageways 601e. The inserted reagent come to contact with the energy excited reactant that pass thorough both filtration passageway 101e and catalyzing passageway 601e and since the reagent is properly energy excited the desired reaction is performed with high probability. Additionally or alternatively, the unstable molecules that were created during the passing through the catalyzing passageways 601e are combined with the inserted reactants.

FIG. 9b illustrates a cross section of die 22 across line CC illustrated in FIG. 9a. Similar to the embodiment of FIG. 3b, die 22 contains five major layers. The bottom layer is substrate 70e, control layer 72e, fluid bottom plane layer 74e, passageway and actuators layer 76e and top layer 78e are fabricated. Control layer 76e may comprise several sub layers. The control layer comprises connecting conductors to the actuators 282. Optionally, the control layer contains connecting conductors 284 to the passageway sensors and/or to the detectors 882.

Control layer 72e, optionally, implement the catalyzer control system and comprises actuator drivers and measurement means including transistors, digital and analogue circuits implemented all implemented inside layer 72e.

Fluid bottom plane layer 74e is preferably made of $SiO_2$ and used as the floor of passageways 101e and 601e.

Passageway and actuators layer 76e contains both the actuators and the passageways structure as illustrated by the top view of FIG. 9a.

The top layer 78e closes the filter passageways from the top side. Layer 78e acts as the ceiling of the passageways and captures the fluid inside the catalyzer cavity.

Figure 10A:
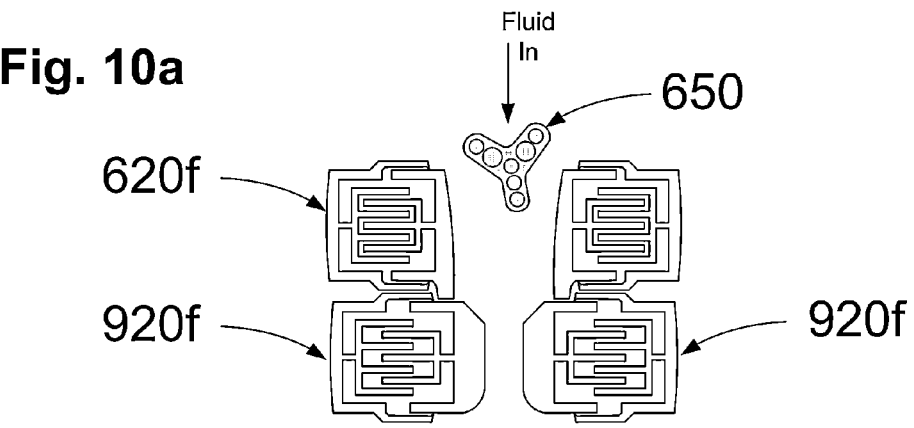
FIG. 10a-10d are focused views of two stage passageway with catalyzing passageway proceed trap passageway in accordance with an exemplary of trap catalyzer embodiment of the current invention.
Figure 10B:
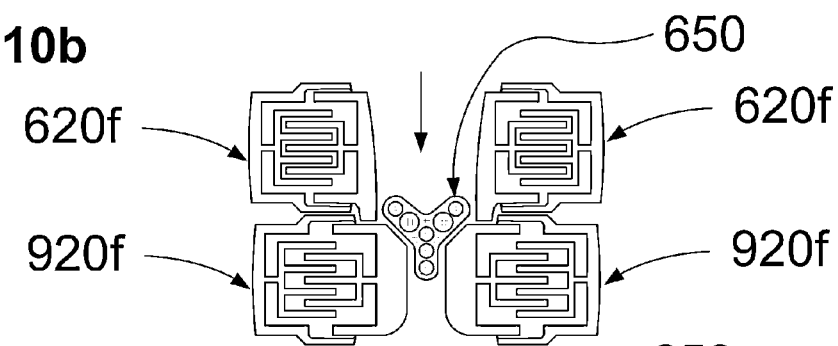
Figure 10C:
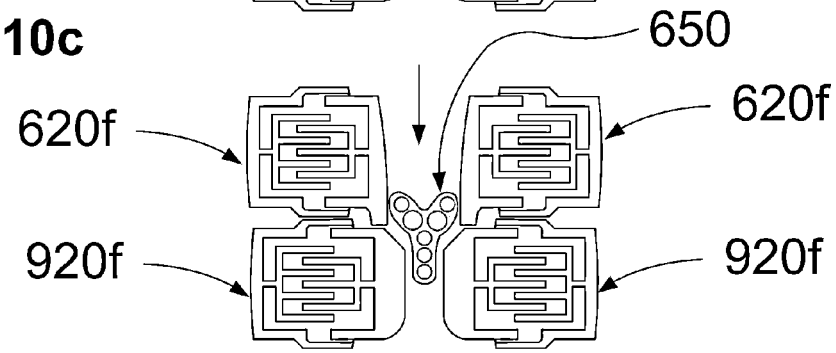
Figure 10D:
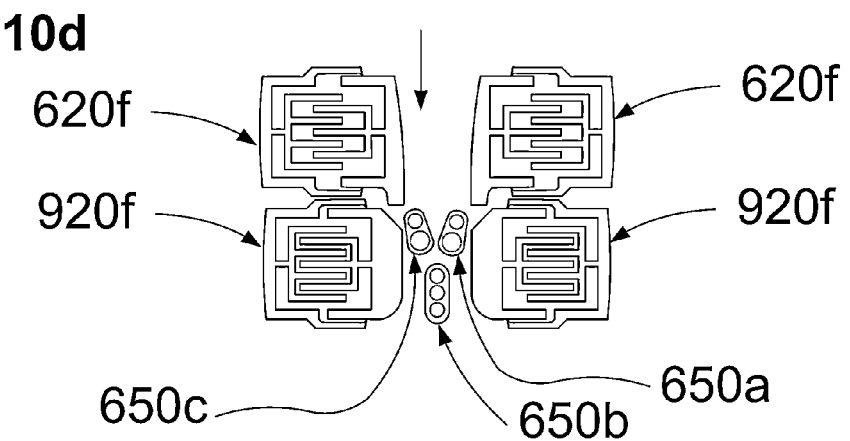

Reference is now made to FIG. 10a-FIG. 10d. FIG. 10a-FIG. 10d are focusing illustrations on a single two stage passageway with catalyzing passageway adjacent to trap passageway. In the figures, catalyzing actuators 620f is located before (in relation to the fluid flow) the trap actuators 920f. Reference is now made to FIG. 10a. In the figure, molecule 650 is approaching the trap. The trap is set so that trap actuators 920f are partially close to allow the head of the molecule enter the trap, while catalyzing actuators 620f are open to allow the molecule body approach the trap. The orientation of the molecule is optionally rotated to the desired orientation using an orientation chamber (not shown in the figure). Reference is now made to FIG. 10b. In FIG. 10b molecule 650 is hold in position by the trap. In FIG. 10c catalyzing actuators 620f close transfer to the molecule body a kinetic energy to promote a chemical reaction. And finally in FIG. 10d trap actuators 920f opens and release the molecule. Since the molecule absorbs the kinetic energy from the catalyzing actuators 620f the molecule breaks down to three product molecules 650a, 650b and 650c.

In an exemplary embodiment of the invention, the actual shape of the edges of catalyzing actuators 620f and trap actuators 920f can be shaped to match the 3D shape of the target molecule.

Figure 11A:
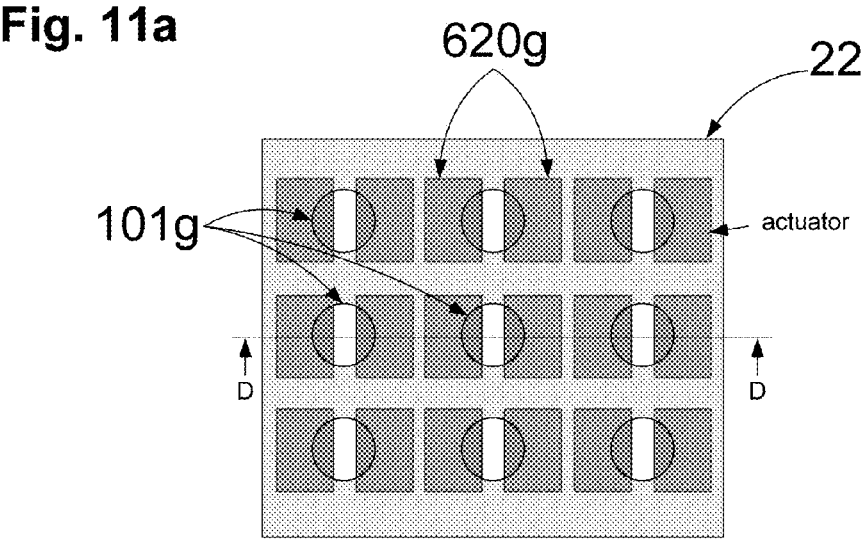
FIG. 11a is a top view of a die in accordance with an exemplary of out of plane catalyzer embodiment of the current invention.
Figure 11B:
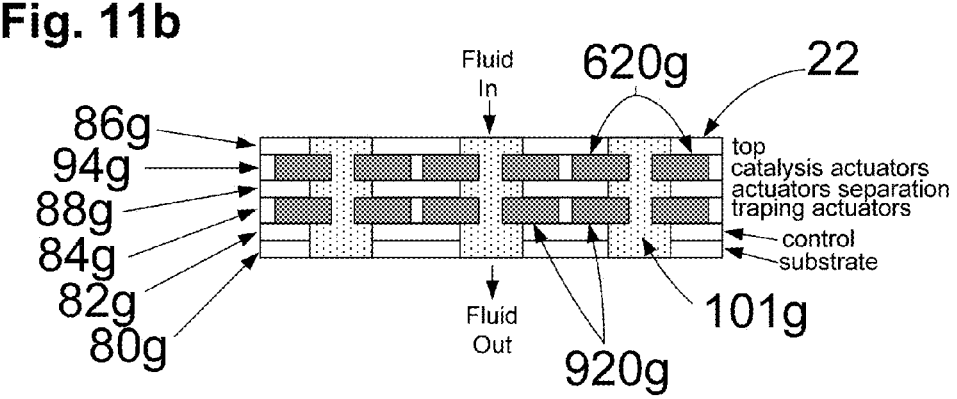

FIGS. 11a-11b illustrate an exemplary simplified embodiment of the catalyzer invention fabricated on a semiconductor die with a perpendicular to die plane implementation.

Reference is made now to FIG. 11a. In FIG. 11a, a top view of the die is illustrated. Similar to the exemplary implementation in FIG. 4, the fluid flows from top of die to the bottom of die perpendicular to the die plane. Die 22 contains a 2D array of passageways 101g. Passageways 101g are fabricated by performing pores through all layers of the die, e.g., by using etching fabrication techniques. The passageway passes through die 12. Each passageway 201 is surrounded by four actuators, two catalyzing actuators 620g and trap actuators 920g (only top two catalyzing actuators 620g are shown in the top view figure). The actuators are organized in two layers: catalyzing layer and trapping layer. Each layer contains a pair of actuator per passageway 101g and each pair can block passageway 101g when the actuators are in close position.

Reference is made now to FIG. 11b. FIG. 3b illustrates a cross section of die 22 across line DD illustrated in FIG. 11a. Die 22 contains six major layers. The bottom layer is substrate 80g. Silicon substrate is preferred but other substrate may be used. Above the substrate, a control layer 82g is fabricated. The details of control layer 82g is similar to control layers 82b and control layer 82d in FIG. 4b and FIG. 6b respectively. The third layer is trapping actuators layer 84g. The actuators in this layer generate the traps. For each passageway 101g two trap actuators 920g are located in this layer. The forth layer is a separation layer 88g that separates between the two actuators layers. The fifth layer is catalyzing actuators layer 94g. For each passageway 101g two catalyzing actuators 620g are located in this layer. The last layer is top layer 86g that protects and holds the sliding actuators and provides passageways 101g inlets. The operation of the catalyzer die 22 is similar to the one illustrated in FIG. 10. First the trap actuators 920g are set and a particle is being trapped. Then, catalyzing actuators 620g provide a kinetic energy and optionally other type of energy (not shown in the figure) to the particle. Finally both trap actuators 920g and catalyzing actuators 620g release the particle and the reaction is performed. Optionally (not shown in the figure) additional energy as well as other reagent are supplied in passageways 101g outlet to complete the reaction.

In an exemplary embodiment of the invention, a LED or Laser, e.g., VCSEL are integrated in the die inside the passageways or inside catalyzing chambers. The LED or Laser emits light to be absorbed by the reactant and effectively promote the desired reaction.

In an exemplary embodiment of the invention, pairs of light emitter such as LED or Laser, e.g., VCSEL and a photo detector are integrated in the die. The light emitting and light detecting pair are used to monitor the existence of a desired particle in the passageways.

The reactions the catalyzer promotes in accordance to the invention are not limited to chemical reaction pre se, rather apply also for break or destroy biological partials, e.g., cells, to grain mineral particle, to bind particle etc.

In an exemplary embodiment of the invention, the number of catalyzing actuators or the number of trapping actuator per passageway can vary from one to many per single trap or passageway. In an exemplary embodiment of the invention, a single trapping or catalyzing actuator is shared between several traps or passageways.

It is appreciated that features described in the embodiments, like trapping, catalyzing, filtration, detection, cleaning, etc. may also be provided in any combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

System Use Examples

The programmability and the versatility of the above described filters or catalyzers can be used in a system where a single device can perform different tasks on time and several devices can work cooperatively either implemented together in the same die or in separate dies.

In an exemplary embodiment of the invention, a sequence of passageway arrays and processing units/elements/subsystems are fabricated on the same die. Several passageway arrays can be located adjacently to each other. Several processing units/elements/subsystems can be located adjacently to each other as well.

Reference now made to FIG. 12. FIG. 12 illustrates a conceptual block diagram of a system containing several filters/catalyzers in a single die. In an exemplary embodiment of the invention, the system die 30 contains nine elements/subsystems, five processing elements 500 and four passageway array 100. Each processing stage might have inlet ports and outlet ports of fluids. Some of those inlets and outlets may be connected to each other either internally on the die or via an external connection. As can be seen two processing subsystem 500 (in stages 3 and 4) are located in series and two passageway arrays 100 are located in series as well. Three a more elements in series are possible. For example system die 30 may implement a blood processing system where the first processing stage is a clogging prevention subsystem that removes all blood cells and big organisms from the blood. Smaller particles flow through the second stage passageway array that set for size that is less then the smallest cell or organism in the blood. Third stage is alignment subsystem for electrical field and fourth stage is clog prevention subsystem for bigger molecules like proteins. Stage 5 and 6 are a trap and a mechanical catalyzer for specific small target molecule in the blood. Stage 7 can inject back the cells that were removed in stage 1. The fluid, with the exited or braked small molecule (and without the protein), pass thorough the passageway array in stage 8. Passageway array in stage 8 is used as a catalyzer and further promote a reaction between the blood cells and the target molecules. In stage 9 the protean are injected back so a closed system for blood processing is illustrated.

In an exemplary embodiment of the invention, particle sorting system is provided using a filter embodiment. At initial state the fluid mixture is provided to the filter when passageway is closed. Then the passageways are gradually opens allow bigger and bigger particle to flow to the filter outlet. The filter outlet synchronously transfers the outlet fluid to different destinations so particle sorting by size is accomplished.

In an exemplary embodiment of the invention, a fluid containing biological particle like blood, plasma or intercellular fluid is inserted to the device in accordance to the invention. The device can first filter the smaller molecule in the fluid then for any particle with size greater then a threshold (set to detect biological particle like cell, virus or bacteria) the device break the particle (a catalysis operation that practically kills the vitality of the organism if it was vital). Such a device can be a sterilizer and with proper setting and several passes of filtration and catalyzing, i.e., breaking, it may used as a selective sterilizer, i.e., sterilizer that kill some organisms but keep other organisms vital.

In an exemplary embodiment of the invention, inlet fluids are sorted and some particle/molecule are brought together in adjacent passageway and together with catalyzing means create new substance in the fluid. In an exemplary embodiment of the invention, a device that takes blood and separate from the blood the glucose from one hand and red blood cell from the other hand. The red blood cells are catalyzed to emit oxygen and then the glucose is promoted to react chemically with the oxygen to provide water and carbon dioxide to the blood. Such a device is a close system, i.e. have only inlet and outlet of blood and the blood that come out of the system have a reduce glucose level. Such a device can be used in vivo in a blood vessel without any need for external reagent port or for external waste port.

It is expected that during the life of a patent maturing from this application many other relevant applications will be developed and the scope of the terms is intended to include all such new technologies a priori.

The terms "comprises", "comprising", "includes", "including", "having" and their conjugates mean "including but not limited to".

As used herein, the singular form "a", "an" and "the" include plural references unless the context clearly dictates otherwise.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method for processing of particles in a fluid comprising:
   (a) providing array of passageways fabricated on a die wherein the passageways comprise:
      a bottom layer;
      a top layer; and
      an actuators layer located therein between,
   the actuators layer further comprises passageway walls connected to actuators, wherein the passageways sizes are controlled by the actuators which move the passageway walls;
   (b) setting said actuators to narrow said passageway size by moving the passageway walls to a size in between a fully open passageway size and a fully closed passageway size in order to perform one of or any combination of (1) filtering of particles, (2) trapping of particles, or (3) catalyzing of particles reaction; and
   (c) stream said fluid through said passageways.

2. A method of claim 1, wherein said array of passageways is partitioned to groups wherein each group is acting in any given time as filter, traps, or catalyzer and the combination between said actuators and said group of passageway are one or more of said actuators are controlling single passageway or a single actuator, alone or together with other actuators, shared plurality of passageways or any other many actuators to many passageways combinations.

3. A method of claim 1, wherein said processing comprises at least one of filtration of particles, sorting of particles, catalysis of particle reactions, clog prevention, particles alignment, particle orientation, energy insertion to particles, reagent insertion, inlets and outlets of fluids or any other fluid processing, wherein said processing is performed using dynamically activating different groups of actuators in time.

4. A method of claim 1, wherein said passageway size is monitored and the actuators controlling the passageway size are activated conditionally upon said passageway size monitoring.

5. A method of claim 1, wherein said passageway size is set by said actuators to be less than said die minimal fabricated passageway size.

6. A method of claim 1, wherein said processing is multistage processing and the processing is performed using multiple arrays of passageway fabricated on the same die and said fluid flows between stages of passageway processing.

7. A method of claim 4, wherein said monitoring is done based on the capacitance measurement between pairs of said passageway walls or on the leakage current measurement between pairs of said passageway walls or on the amount of light or any electromagnetic signal with different wavelength that pass thorough the passageway or on any other measurable physical property that change its value with passageway size.

8. A method of claim 1, wherein said actuators are MEMS actuators based on electrostatic, electromagnetic or piezoelectric forces.

9. A method of claim 1, wherein said die is multilayer die and the layers are fabricated using at least one of evaporation, photolithography and etching.

10. A method of claim 1, wherein said passageways are fabricated in one or more layers of said die or fabricated across all layers perpendicular to the plane of said die.

11. A method of claim 1, wherein said processing comprises either particle alignment processing or particle orientation processing or both using the mean of (1) electric field, (2) magnetic field, (3) mechanical structures or (4) mechanical forces or any combination thereof.

12. A method of claim 1, wherein said trapping particles by said passageways is performed by setting the passageway size to enable partial entry of a target particle to said passageway or performed by reducing the passageway size when a target particle is inside the passageway.

13. A method of claim 1, wherein said processing comprises particle energy insertion and wherein the energy supplied to said particle at least in the form of kinetic energy, electric energy, magnetic energy, electromagnetic energy, heat energy or a combination of these.

14. A method of claim 13, wherein said actuators are delivering said kinetic energy to said particles.

15. A method of claim 1, wherein said die comprises particles detectors located in said passageways or adjacent to said passageways inlet or outlet.

16. A method of claim 6, wherein said multistage processing comprises a stage of trapping and a stage of catalyzing and wherein the stage of catalyzing is performed after a particle is being trapped.

17. A method of claim 6, wherein said multistage processing comprises a stage of trapping of a biological particle or a cell or an organism and a stage of catalyzing that destroy or kill said biological particle or cell or organism.

* * * * *